United States Patent [19]
Thiberg

[11] Patent Number: 5,766,233
[45] Date of Patent: Jun. 16, 1998

[54] DEVICE FOR WOUND HEALING BY MEANS OF LIGHT

[75] Inventor: Rolf Thiberg, Åkersberga, Sweden

[73] Assignee: Biolight Patent Holding AB, Danderyd, Sweden

[21] Appl. No.: 676,217

[22] PCT Filed: Jan. 19, 1995

[86] PCT No.: PCT/SE95/00048

§ 371 Date: Jul. 18, 1996

§ 102(e) Date: Jul. 18, 1996

[87] PCT Pub. No.: WO95/19809

PCT Pub. Date: Jul. 27, 1995

[30] Foreign Application Priority Data

Jan. 20, 1994 [SE] Sweden .................. 9400153

[51] Int. Cl.⁶ .................................. A61N 5/00
[52] U.S. Cl. .................................. 607/88
[58] Field of Search .................. 607/88, 89, 100, 607/2, 50; 606/1, 3, 9, 10–13, 16; 315/174, 324, 246, 200

[56] References Cited

U.S. PATENT DOCUMENTS 4,930,504 6/1990 Diamantopoulos et al. ........... 128/395
5,259,380 11/1993 Mendes et al. ........... 607/115

*Primary Examiner*—Jennifer Bahr
*Assistant Examiner*—Rosiland Kearney
*Attorney, Agent, or Firm*—Alfred J. Mangels

[57] ABSTRACT

A device for healing wounds and sores with the aid of light, including a light emitting element which is intended to lie against or be held close to a wound or sore on the body of an individual, and a drive arrangement for driving the light emitting element, wherein the light emitting element includes light emitting diodes or like devices and is constructed to emit infrared light. The drive arrangement (8, 9, 19) is constructed to cause the light emitting element (1) to emit infrared light in a first stage for a first predetermined length of time and thereafter to emit visible red light in a second stage for a second predetermined length of time. The drive arrangement (8, 9, 10) is also constructed to cause the light emitting element (1) to pulsate the emitted infrared light and the emitted red light respectively in accordance with a predetermined series of pulse frequencies over the predetermined time periods.

13 Claims, 1 Drawing Sheet

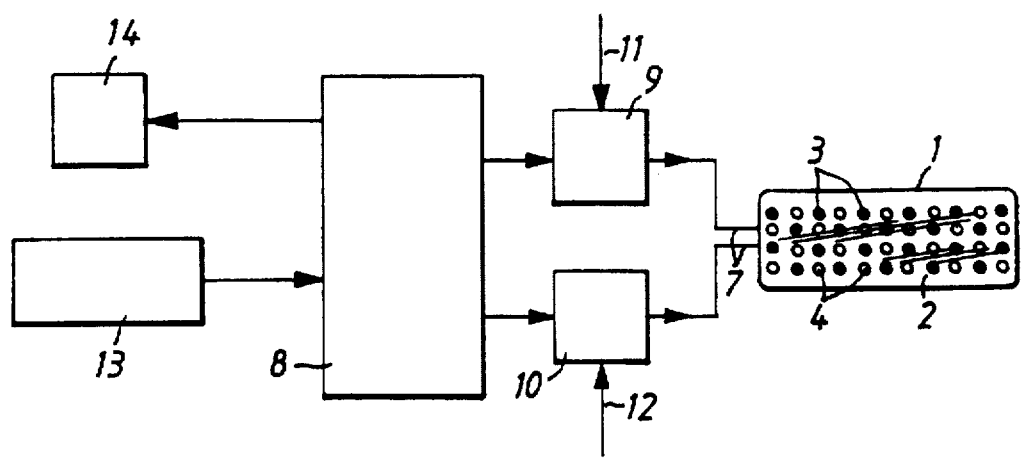
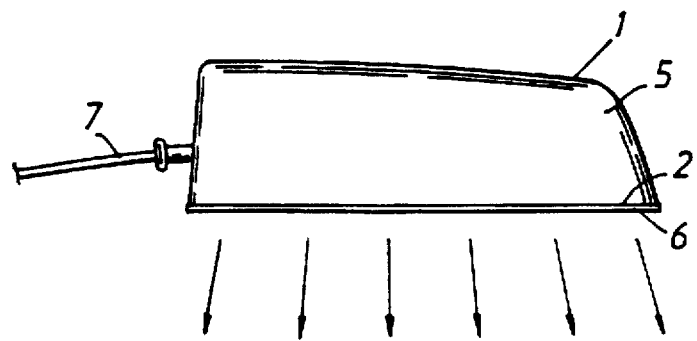

DEVICE FOR WOUND HEALING BY MEANS OF LIGHT

BACKGROUND OF THE INVENTION

1. FIELD OF THE INVENTION

The present invention relates to a device for healing wounds and sores with the aid of light, where, more specifically, the light facilitates healing of the wound or sore and accelerates the healing process.

2. DESCRIPTION OF THE RELATED ART

It has been found that the treatment of wounds and sores with the aid of light has a favorable effect on the healing process, such as to accelerate healing. This applies to both wounds in the form of continuity interruptions in normal tissue and such sores as pressure sores caused by violence, leg ulcers, burn injuries, etc.

It has been observed that infrared light has a favorable effect on the healing of wounds and sores.

SUMMARY OF THE INVENTION

The present invention is based on the understanding that light treatment effected by transmitting given light at given time intervals will give a significantly improved effect in the form of a shortened healing time. The present invention enables the time taken to heal a wound or sore to be halved in all essential in comparison with a healing process in which no treatment is given.

The present invention thus relates to a device for healing wounds and sores with the aid of light, this device including a light emitting element which is intended to lie against or be held close to a wound or sore on the body of an individual, and a means for powering the light emitting element. The light emitting element includes light emitting diodes or the like and is intended to emit infrared light. The power means is constructed to cause the light emitting element to emit infrared light in a first stage for a first predetermined length of time, and thereafter to cause the light emitting element to emit visible red light in a second stage for a second predetermined length of time. The power means is also constructed to cause the light emitting element to pulsate the emitted infrared light and the visible red light respectively in accordance with a predetermined series of pulse frequencies over said predetermined time periods.

BRIEF DESCRIPTION OF THE DRAWINGS

The invention will now be described in more detail, partly with reference to an exemplifying embodiment of the invention illustrate in the accompanying drawing, in which FIG. 1 is a block schematic illustrating the device, and FIG. 2 is a side view of a light emitting element.

DESCRIPTION OF THE PREFERRED EMBODIMENTS

FIGS. 1 and 2 illustrate a device for healing wounds and sores with the aid of light, said device including a light emitting element 1 which is intended to be placed against or held close to a wound or sore on the body of an individual. The light emitting element is shown from one side in FIG. 2 and from beneath in FIG. 1. This member includes a housing 5 which is provided with a transparent plate 6. Above the plate 6 there is located a surface 2 in which a number of light emitting diodes 3, 4 or corresponding devices are mounted. Thus, the light emitting diodes are intended to transmit light through the plate 6 when activated, i.e. when supplied with current through a cable 7. In use, the housing 5 is held so that the plate 6 will lie against the part of the body to be treated. The device also includes drive means 8, 9, 10 for driving the light emitting element 1. The light emitting element 1 includes light emitting diodes 3 or like devices which are constructed to emit infrared light. These diodes are marked with solid circles in FIG. 1.

According to the invention the drive means are provided to cause the light emitting element 1 to emit infrared light in a first stage for a first predetermined length of time, and then to emit visible red light in a second stage for a second predetermined length of time. Visible red light is emitted by means of light emitting diodes 4 or like devices. These devices are marked with hollow circles in FIG. 1. It is extremely important that the treatment is carried out in the order infrared light followed by visible light.

According to the present invention, the drive means are also constructed to cause the light emitting element 1 to pulsate the emitted infrared light and the visible red light respectively in accordance with a predetermined series of pulse frequencies over the aforesaid predetermined time periods.

The drive means include a computer 8 and associated memory, and drive circuits 9, 10 which are controlled by the computer. These drive circuits 9,10 are supplied with voltage for powering the light emitting diodes 3, 4, through conductors 11, 12. One drive circuit, 9, is intended to activate the infrared light emitting diodes 3 and the other drive circuit 10, is intended to activate the light emitting diodes 4 that emit visible red light. The computer and the drive circuits are of a suitable known kind.

The infrared light emitting diodes 3 are preferably GaAs-type semi-conductors (gallium arsenide) which emit light having a wavelength of 950 nanometers. The light emitting diodes 4 which emit visible light are preferably of the GaAs-type which emit light having a wavelength of 660 nanometers.

According to one preferred embodiment of the invention, the light emitting diodes are present in the light emitting element in such numbers that the infrared light emitting diodes together deliver a light power of 900 milliwatts, while the visible red light emitting diodes together deliver a light power of 3000 millicandela.

Mention is made in the aforegoing of predetermined lengths of times over which light is emitted during a treatment. According to one preferred embodiment, these predetermined time periods are approximately of equal duration. Furthermore, the predetermined time period lies in a range of 2–4 minutes, preferably 3 minutes.

Mention is made in the aforegoing of a series of pulse frequencies. According to one preferred embodiment, each series is comprised of three mutually sequential pulse frequencies at which respective light is emitted.

In summary, this means that there is first emitted solely infrared light, said light being emitted so as to be pulsed in a manner such that there is first emitted light which is pulsed at a given pulse frequency, whereafter the light is emitted while pulsed at a second pulse frequency, and then at a third pulse frequency. Thereafter there is emitted only visible red light, this light being pulsed at a first pulse frequency and then at a second pulse frequency and thereafter at a third pulse frequency.

Provided that the predetermined time period is three minutes, infrared light is emitted over a period of three minutes, and is then followed by visible red light over a period of three minutes. Preferably, the duration of each pulse frequency in the series is one minute.

According to a highly preferred embodiment of the invention, the first series of pulse frequencies is 78±10 Hz, 702±20 Hz and 8.58 KHz ±100 Hz. The infrared light is thus first pulsed at a pulse frequency of 78 Hz, followed by a pulse frequency of 702 Hz and then at a pulse frequency of 8.58 KHz, whereafter visible red light is emitted in accordance with the same pulse frequency series.

A typical treatment of a wound or sore is effected by turning the light emitting element to face the wound or sore and infrared light is emitted in accordance with the aforesaid series for a total period of three minutes, whereafter visible red light is also emitted in accordance with said series for a total period of three minutes. Treatment thus takes six minutes. The treatment is repeated from two to three times each week. Typically, the effect of the treatment will be seen after 4–6 treatments.

According to one preferred embodiment, the infrared light and the visible red light respectively are emitted in accordance with another pulse frequency series after from 4 to 6 treatments using the aforementioned series. According to this embodiment, the drive means 8, 9, 10 is intended to cause the light emitting element 1 to emit a second series of pulse frequencies, this second pulse frequency series being, 15.6±3 Hz, 287±20 Hz and 31.2±5 Hz. Each type of light is preferably emitted for a total period of three minutes also with this second pulse frequency series.

In the aforegoing, pulse frequency series have been mentioned in which the pulse frequency is given a relatively narrow interval. It is important that the pulse frequency is the nominal frequency or very close thereto. However, the aforesaid predetermined time periods can be varied slightly.

Connected to the computer 8 is a keyboard 13 by means of which relevant series and the duration of said series can be chosen by depressing the appropriate keys. There will preferably be found a number of different preprogrammed treatment programs to choose from. To the computer 8 there is also connected a display 14 which presents desired data, such as the treatment program chosen, the time duration of the series, etc.

It will be understood that the construction of the light emitting element can be changed, and that the number and the power of the light emitting diodes can also be changed. The control circuit that includes the computer can also be modified.

The present invention cannot therefore be considered restricted to the aforedescribed embodiments, since the variations and modifications can be made within the scope of the following claims.

What is claimed is:

1. A device for providing light for healing wounds and sores, said device comprising:
   a) a light emitting element for positioning adjacent a wound or sore on the body of a person, the light emitting element including a source of infrared light and a source of visible red light; and
   b) drive means for driving the light emitting element, the drive means including a timer for causing the light emitting element to emit only infrared light during a first treatment stage for a first predetermined period of time and thereafter to emit only visible red light during a second treatment stage for a second predetermined period of time, and including pulsation means for pulsating the emitted infrared light and the emitted visible light at a predetermined series of pulsation frequencies over the respective time periods, wherein the first and second predetermined time periods are of substantially equal duration.

2. A device according to claim 1 wherein the predetermined time periods are each between 2–4 minutes.

3. A device according to claim 1 wherein each of said series of pulse frequencies includes three sequential pulse frequencies at which light is emitted.

4. A device according to claim 3 wherein a first series of pulse frequencies is 78±10 Hz, 702±20 Hz and 8.58 KHz±100 Hz.

5. A device according to claim 4 wherein the drive means causes the light emitting element to emit a second series of pulse frequencies for transmission after a wound or sore has been treated with the first series of pulse frequencies from four to six times, the second series of pulse frequencies being 15.6±3 Hz, 287±20 Hz, and 31.2±5 Hz.

6. A device according to claim 1 wherein the light emitting element includes infrared light emitting diodes which emit light having a wavelength of about 950 nanometers.

7. A device according to claim 6 wherein the infrared light emitting diodes together produce a total light power of about 900 milliwatts, and wherein the light emitting element includes visible red light emitting diodes that together produce a total light intensity of about 3000 millicandela.

8. A device according to claim 1 wherein the light emitting element includes red light emitting diodes which emit visible light having a wavelength of about 660 nanometers.

9. A device according to claim 8, wherein the light emitting element includes infrared light emitting diodes that together produce a total light power of about 900 milliwatts, and the visible red light emitting diodes together produces a total light intensity of about 3000 millicandela.

10. A device according to claim 1 wherein the source of infrared light and the source of visible red light are both light emitting diodes.

11. A device according to claim 1 wherein the light emitting element includes infrared light emitting diodes which emit light having a wavelength of about 950 nanometers, and visible red light emitting diodes which emit light having a wavelength of about 660 nanometers.

12. A device according to claim 1, wherein the predetermined time periods are 3 minutes.

13. A device according to claim 1, wherein the drive means includes a first drive circuit for activating the infrared light source and a second drive circuit for activating the visible red light source.

* * * * *